US009254366B2

(12) United States Patent
Matthias

(10) Patent No.: US 9,254,366 B2
(45) Date of Patent: Feb. 9, 2016

(54) NEEDLE ASSEMBLY AND MEDICATION DELIVERY SYSTEM

(75) Inventor: Claudia Matthias, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 1172 days.

(21) Appl. No.: 13/131,515

(22) PCT Filed: Dec. 17, 2009

(86) PCT No.: PCT/EP2009/067393
§ 371 (c)(1),
(2), (4) Date: Jul. 28, 2011

(87) PCT Pub. No.: WO2010/072644
PCT Pub. Date: Jul. 1, 2010

(65) Prior Publication Data
US 2011/0276008 A1 Nov. 10, 2011

(30) Foreign Application Priority Data
Dec. 23, 2008 (EP) .................... 08022375

(51) Int. Cl.
A61M 5/00 (2006.01)
A61M 5/34 (2006.01)
A61M 5/24 (2006.01)
A61M 5/31 (2006.01)

(52) U.S. Cl.
CPC ............... A61M 5/34 (2013.01); A61M 5/2466 (2013.01); A61M 5/24 (2013.01); A61M 5/3146 (2013.01); A61M 2005/2407 (2013.01)

(58) Field of Classification Search
CPC ............ A61M 5/3146; A61M 5/2466; A61M 5/3202; A61M 2005/2474; A61M 2005/3204; A61M 5/34
USPC .......................................... 604/192, 198, 139
See application file for complete search history.

(56) References Cited

U.S. PATENT DOCUMENTS 3,375,825 A * 4/1968 Keller ........................... 604/193
3,825,003 A    7/1974 Kruck
4,378,015 A * 3/1983 Wardlaw ....................... 604/137

(Continued)

FOREIGN PATENT DOCUMENTS

FR    2278350        2/1976
WO    97/36624       10/1997
WO    03/057289      7/2003

OTHER PUBLICATIONS

European Search Report for European patent application No. EP 08022375, dated May 11, 2009.

(Continued)

Primary Examiner — Bhisma Mehta
Assistant Examiner — Bradley Osinski
(74) Attorney, Agent, or Firm — Fish & Richardson P.C.

(57) ABSTRACT

A needle assembly has distal and proximal ends. The needle assembly comprises a body element having distal and proximal ends, an attachment means configured to be attached to a medication delivery device, a button element which is movable from a first position to a second position, and a needle configured to move to the distal direction, when the button element is moved from the first position to the second position.

15 Claims, 3 Drawing Sheets

(56) References Cited

U.S. PATENT DOCUMENTS

| | | | | |
|---|---|---|---|---|
| 6,898,991 B2 * | 5/2005 | Geise | ............... | G01N 1/02 73/864.52 |
| 2011/0276008 A1 * | 11/2011 | Matthias | ............... | 604/201 |

OTHER PUBLICATIONS

International Search Report for PCT patent application No. PCT/EP2009/067393, mailed Apr. 1, 2010.

* cited by examiner

NEEDLE ASSEMBLY AND MEDICATION DELIVERY SYSTEM

CROSS REFERENCE TO RELATED APPLICATIONS

The present application is a U.S. National Phase Application pursuant to 35 U.S.C. §371 of International Application No. PCT/EP2009/067393 filed Dec. 17, 2009, which claims priority to EP Patent Application No. 08022375.3 filed on Dec. 23, 2008. The entire disclosure content of these applications are herewith incorporated by reference into the present application.

TECHNICAL FIELD

The invention concerns a needle assembly for a medication delivery device and a medication delivery system comprising the needle assembly and the medication delivery device.

BACKGROUND

A medication delivery device may comprise a housing containing a cartridge which contains medication. A membrane may be located at the distal end of the cartridge and a bung may be located at the proximal end of the cartridge. A delivery needle assembly, which comprises a needle, may be attached to the housing so that the needle punctures the membrane. The medication can be expelled through a needle of the delivery needle assembly. A drive mechanism of the medication delivery device is configured to push the bung along the cartridge so that the medication is expelled through the needle. The delivery needle assembly is suitable to administer the medication to a patient.

The drive mechanism may comprise a piston which pushes the bung to the distal direction. When a predetermined dose of medication is delivered, the piston moves in the distal direction, wherein the piston moves forward a distance which corresponds to the predetermined dose value. The bung should move forward the same distance to ensure that the predetermined dose value is delivered. However, the piston may not lie against the bung before first use. In this case the distance of the piston would not correspond with the distance of the bung, so that a wrong dose would be delivered. First use means use of the medication delivery device to administer a first dose from the cartridge to the patient.

Prior to first use of the medication delivery device, the user should prime the medication delivery device. Priming means that a priming dose is delivered before first use. The priming dose is not injected to the patient. The priming dose value may be less than a dose value which is injected to the patient. After priming the piston lies against the bung, so that the correct to dose can be delivered.

Some users fail to prime the medication delivery device before use. It is an aim of the invention to provide means for overcoming this.

SUMMARY

For this purpose a needle assembly is provided. The needle assembly has a distal end and a proximal end. The needle assembly comprises a body element having distal and proximal ends, an attachment means configured to be attached to a medication delivery device, a button element which is movable from a first position to a second position, and a needle configured to move to the distal direction when the button element is moved from the first position to the second position.

The needle assembly is suitable to prime the medication delivery device before first use, as explained later.

One embodiment of the medication delivery device is a pen-type medication delivery device which is suitable to provide several doses of medication. In one embodiment the dose value is fixed. In an alternative embodiment the dose value can be adjusted by the user. The pen-type medication delivery device may be used to administer insulin, heparin and any other liquid or gel medication.

One embodiment the medication delivery device comprises a housing, which contains a cartridge. A membrane is located at the distal end of the cartridge and a bung is located at the proximal end of the cartridge.

Before first use of the medication delivery device a priming dose should be delivered. For this purpose, the medication in the cartridge is provided in a pressurised manner. Alternatively, the user pressurises the medication in the cartridge by means of the delivery mechanism so that the piston is pushed towards the bung element, so that the medication in the cartridge is pressurised.

When the medication delivery device is being primed, medication is discharged so that the pressure in the cartridge is relieved. For this purpose, the needle of the needle assembly punctures the membrane of the cartridge. The amount of medication which is sufficient to relieve the pressure of the cartridge is discharged through the needle.

The first position of the button element is a starting position of the button element in the initial state before priming. The button element reaches the second position during the priming process. The second position is not necessarily the position of the button element at the end of the priming process. In one embodiment the button element is rotationally moved. In one embodiment the button element is moved in the distal direction.

Preferably, the needle assembly comprises a medication trapping means suitable to trap the medication which is delivered through the needle. More preferably, the medication trapping means is formed as a tank surrounding a distal part of the needle. The tank provides sufficient space for medication which is delivered during the priming process. An alternative embodiment of the medication trapping means is made of an absorptive material.

In one embodiment of the needle assembly, the attachment means is locked in a first state and the attachment means is unlocked in a second state. The first state is an initial state, wherein the needle assembly is attached to the medication delivery device before first use of the medication delivery device. The needle assembly cannot be removed until priming has been performed by the needle assembly. In the second state, after priming, the needle assembly is unlocked so that it can be detached from the medication delivery device.

One embodiment of the attachment means is formed as snapping means. The snapping means is elastic and suitable to engage with the medication delivery device in a form-fitting manner. In the first state the snapping means engages with the medication delivery device so that the needle assembly is attached to the medication delivery device by means of a snapping connecting. In the second state the elastic snapping means is bent, so that the priming needle assembly is detachable.

In one embodiment, the needle assembly comprises a resistance element which is configured to counteract against the movement of the button element. The resistance element slows down the priming process. Thus, there is sufficient time for discharging medication so that the pressure of the cartridge is relieved. In one embodiment, the resistance element is configured to counteract against a distal movement of the button element when the needle reaches a first predetermined position. The needle may reach the first predetermined position after puncturing the membrane of the cartridge which is located inside the medication delivery device. In other words, as long as a force which impacts to push the button element is needed for puncturing the membrane the movement of the button element is not counteracted. After the membrane has been punctured, the movement speed of the button element is slowed down. Preferably, the resistance element is formed as spring element. In an alternative embodiment, friction counteracts against the movement of the button element.

In one embodiment, the attachment means is unlocked when the button element reaches a second predetermined position. Preferably, the button element interacts with the attachment means so that the needle assembly can be detached from the medication delivery device when the button element has been moved to the second predetermined position. In one embodiment the second predetermined position is the position the button element reaches at the end of the priming process. The button element may reach the end position when the spring element is completely compressed.

In one embodiment the body element has a distal part and a proximal part which forms the attachment means. The attachment means is located at the distal end of the needle assembly. The button element is located at the proximal end of the needle assembly. In one embodiment the button element can be pushed to the distal direction with respect to the body element.

In one embodiment, the button element can be at least partly inserted to the body element. A stopping means is provided for stopping the movement of the body element, the stopping means being formed as protrusion located on the inside wall of the body element.

A medication delivery system comprises the medication delivery device and the needle assembly, which is described here, the needle assembly being attached to the medication delivery device.

One embodiment of the medication delivery device comprises a needle hub and a cartridge containing medication and having a membrane. The needle hub is releasably connected with the attachment means. The needle assembly is attached to the needle hub before first use of the medication delivery device. The needle assembly is detachable in the second state, after priming.

In the first state the snapping means engages with needle hub. Therefore the needle assembly can not be detached. In the second state, after priming, the snapping means disengages from the needle hub so that the needle assembly is detachable. After detachment the medication delivery device can be used for administering the medication to the patient.

In one embodiment of the medication delivery system, the needle does not puncture the membrane if the button element is in the first position. The needle punctures the membrane when the button element is moved to the second position for priming.

Other features will become apparent from the following detailed description when considered in conjunction with the accompanying drawings.

DETAILED DESCRIPTION

Figure 1:
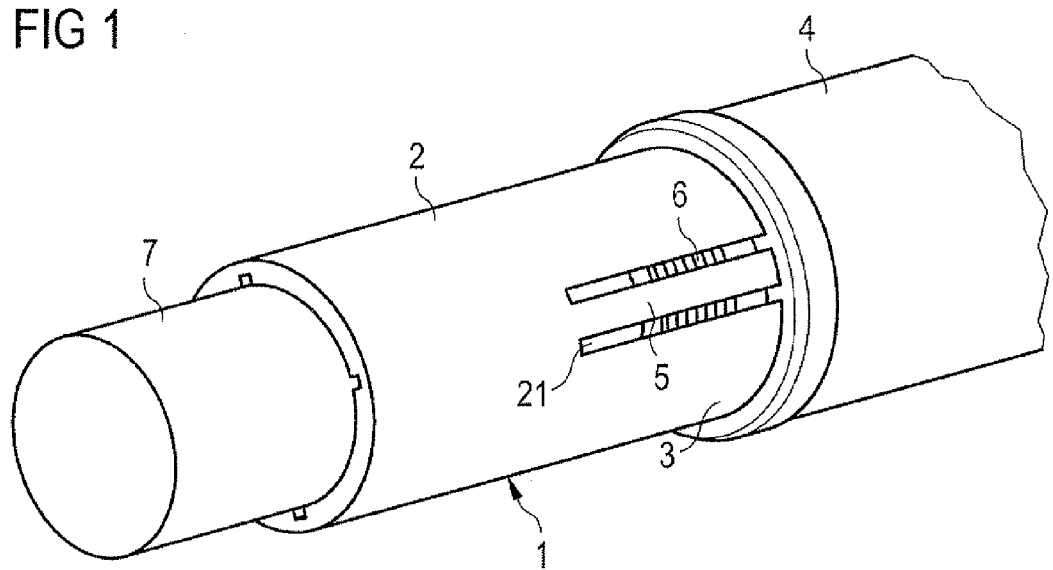
FIG. 1 shows a perspective representation of a needle assembly which is attached to a distal part of a pen-type medication delivery device.

FIG. 1 shows a perspective representation of a needle assembly which is attached to a distal part of a pen-type medication delivery device.

The pen-type medication delivery device 4 contains medication and is suitable to deliver a multitude of doses of the medication. A delivery needle assembly (not shown) is attached to a needle hub 6 of the pen-type medication delivery device 4 before medication delivery to a patient. The delivery needle assembly is configured to inject the medication to the body of the patient. The needle hub 6 is located at the distal end of the medication delivery device 4.

The medication is contained in a cartridge (15, not shown in FIG. 1) which is located in a distal part of the medication delivery device 4. A distal part of the cartridge is covered by a membrane (16, not shown in FIG. 1). A bung (not shown) is located at the proximal end of the cartridge.

A drive mechanism (not shown) of the medication delivery device is configured to push the bung to the distal direction along the cartridge so that the medication is expelled through the needle (not shown).

The drive mechanism may comprise a piston (not shown) which pushes the bung to the distal direction. When a predetermined dose of medication is delivered, the piston moves distally, wherein the distance the piston moves forward corresponds to the dose value. The bung should move forward the same distance to ensure that the predetermined dose value is delivered.

However, the piston may not lie against the bung before first use of the medication delivery device. In this case the distance of the piston would not correspond with the distance of the bung, so that a wrong dose would be delivered.

Priming should be performed before first use of the medication delivery device. For this purpose the medication in the cartridge is pressurised. In one embodiment the piston is pushed towards the bung which slightly moves forward so that the medication inside the cartridge is pressurized. In one embodiment the user pressurises the medication before priming, e.g. by moving the piston towards the bung element by means of the drive mechanism. In an alternative embodiment the manufacturer provides a medication delivery device wherein the medication in the cartridge is pressurised.

The needle assembly 1 primes the pen-type medication delivery device. Priming means that medication is delivered into the needle assembly 1 so that the pressure of the cartridge is relieved.

Preferably, the medication delivery device 4 is provided with the needle assembly 1, which is attached to the needle hub 6 of the medication delivery device 4. The presence of the needle assembly 1 calls the user's attention to priming the medication delivery device 4 before first use. In an alternative embodiment the needle assembly 1 is attached to the medication delivery device 4 by the user before first use.

The needle assembly 1 has distal and proximal ends. The distal end is attached to the medication delivery device 4.

The needle assembly 1 comprises a body element 2 having a distal part which is formed as attachment means 3 configured to attach the needle assembly 1 to the needle hub 6 of the medication delivery device 4.

The attachment means 3 comprises elongated elastic snapping means 5 which are configured to engage with the needle hub 6 of the medication delivery device 4.

A button element 7 is located at the proximal end of the body element 2. When the button element 7 is pushed to the distal direction with respect to the body element 2 the medication delivery device 4 is primed, as described later.

Figure 2:
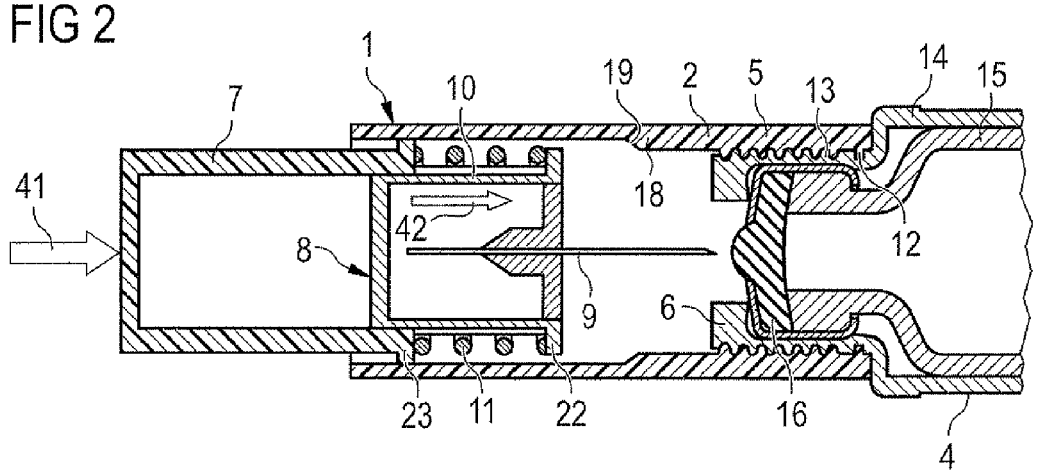
FIG. 2 shows a section of the needle assembly which is attached to a needle hub of the medication delivery device.

FIG. 2 shows a section of the needle assembly 1, which is attached to the needle hub 6 of the medication delivery device 4.

The medication delivery device 4 has distal and proximal ends. The distal end of the medication delivery device 4 is attached to the distal end of the needle assembly 1.

The medication delivery device 4 comprises a housing 14 containing a cartridge 15 which is filled with the medication. The distal part of the cartridge 15 is covered by a membrane 16.

The distal end of the housing 14 is designed as needle hub 6 comprising a thread 13 which is configured to be connected with a thread of a delivery needle assembly (not shown). The delivery needle assembly is used to inject the medication to the patient.

A groove 12 is located in the needle hub 6. The groove 12 is configured to be engaged with a joint part 20 of the snapping means 5 of the needle assembly 1. In this embodiment the groove 12 extends circumferentially. In an alternative embodiment (not shown) a cavity is provided, the cavity being configured to be engaged with the joint part 20.

The body element 2 of the needle assembly 1 is formed as hollow cylinder. The distal end of the body element 2 is formed as attachment means 3. The cylindrically formed attachment means 3 is configured to be placed over the needle hub 6. Two parallel incisions (21, shown in FIG. 1) which axially extend from the distal end of the body element 2 to an inner part of the body element 2 form an elongated snapping means 5. The snapping means 5 is elastic. This embodiment comprises two snapping means 5 which are arranged opposite to each other. Alternative embodiments comprise more snapping means or less snapping means.

The snapping means 5 comprises a joint part 20 located at the distal end of the snapping means 5, the joint part 20 is configured to engage with the groove 12 of the needle hub 6, when the needle assembly 1 is attached to the needle hub 6. In an initial state before priming, the joint part 20 engages with groove 12 of the needle hub 6. In this embodiment the groove is provided additionally to the thread 13 of the needle hub 6. In an alternative embodiment (not shown) the snapping means 2 engages with the thread 13 of the needle hub 6.

A mating means 18 which is formed as protrusion on the inside wall of attachment means 3 is located at the proximal end of the snapping means 5, the mating means 18 having a chamfer 19. The snapping means 5 is configured to be bent away from the body element 2 in a radial direction, when an element distally moves towards the chamfer 19, so that the protrusions are pushed outwards resulting in radial movement of the snapping means 5 and the joint part 20.

A needle unit 8 is located inside the body element 2. The needle unit 8 comprises a needle 9 having distal and proximal ends and a medication trapping means 10 which is formed as cylinder-shaped tank surrounding the proximal end of the of needle 9 so that medication dispensed by the needle 9 is trapped inside the tank. The needle 9 is fixed to the tank.

The needle unit 8 is axially moveable inside the body element 1. In the initial state the needle 9 does neither touch nor puncture the membrane 16 of the medication delivery device 4. The needle unit 8 is configured to move along the mating means 18 without being stopped by the mating means 18. In one embodiment the diameter of the needle unit 8 is dimensioned so that the needle unit 8 and the mating means 18 do not interact. In one embodiment the side wall of the needle unit 8 has a trench which is formed so that the mating means 18 is located inside the trench, when the needle unit 8 moves along the mating means 8.

The button element 7 is located at the proximal end of the body element 2. In the initial state, a distal part of the button element 7 is inserted to the body element 2. A proximal part of the button element 7 protrudes from the distal end of the body element 2.

The button element 7 is formed as hollow cylinder having a distal wall. The proximal end of the medication trapping means 10 is inserted to the distal end of the button element 7.

The button element 7 is distally movable with respect to the body element 2 and distally movable with respect to the needle unit 8.

A spring element 11 extends along the outside wall of the medication trapping means 10. The spring element 11 is located in the chamber formed by the outside wall of the medication trapping means 10, the inner wall of the body element 2, a distal edge 23 of the button element and a distal edge 22 of the needle unit. A distal end of the spring element 11 is located adjacent to the distal edge 22 of the needle unit. A proximal end of the spring element 11 is located adjacent to the distal edge 23 of the button element. The spring element 11 is configured to be compressed by the distal edges 22, 23 of the needle unit and the button element when the button element 7 moves in the proximal direction with respect to the needle unit 8. In the initial state the spring element 11 is not compressed.

Operation of the priming needle assembly 1 is explained in the following.

During priming the user pushes the button element 7. In other words, an external pushing force, as indicated by arrow 41, impacts to the proximal wall of the button element 7. When the button element 7 is pushed, it moves to the distal direction with respect to body element 2. The distal movement of the button element 7 is transferred to the needle unit 8 via the spring element 11.

The spring element 11 is compressed when a first force impacts proximally to the distal end of the spring element 11 and a second force impacts distally to the proximal end of the spring element 11. Though the pushing force 41 impacts distally to the proximal end of the spring element 11, the spring element 11 is not compressed because there is no force which impacts to the proximal direction. Thus, the force 41 is transferred via the spring element 11 to the needle unit 8, which moves distally with respect to the body element 2 as indicated by an arrow 42.

A small counterforce may impact proximally to the needle unit 8, wherein the counterforce may be caused by friction between the needle unit 8 and the body element 2. However, the counterforce may cause a slightly compression of the spring element 11 at the most, but the needle unit 8 moves to the distal direction with respect to the body element 2 when the button element 7 moves to the distal direction with respect to the body element 2.

When the needle unit 8 moves distally with respect to the body element 2, the distal part of the needle 9 punctures the membrane 16 of the cartridge 15. Puncturing the membrane 16 provides a counterforce which impacts distally to the needle unit 8. Due to the stiffness of the spring element 11 the counterforce is not sufficient to compress the spring element 11 significantly. Thus, the distal part of the needle 9 moves through the membrane 16 when the button element 7 is moved further to the distal direction with respect to the body element 2.

When the needle 9 has punctured the membrane 16, the medication is delivered through the needle 9 due to the pressure in the cartridge 15. The medication is delivered to the medication trapping means 10 until the pressure of the cartridge 15 is relieved or the needle 9 is extricated from the membrane 16.

The needle unit 8 moves to the distal direction with respect to the body element 2 until the distal end of the needle unit 8 reaches the top of the needle hub 6, which stops the movement of the needle unit 8.

Figure 3:
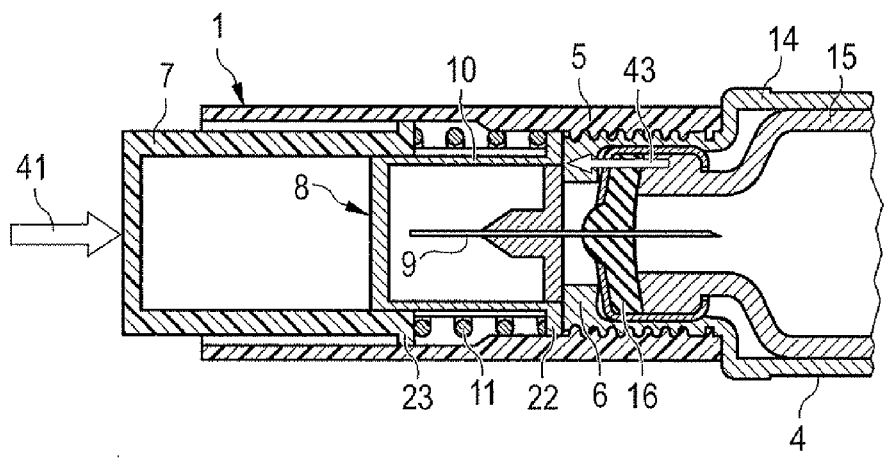
FIGS. 3 to 5 show the section of the needle assembly during operating the needle assembly.

FIG. 3 shows the priming needle assembly 1, wherein the needle unit 6 has reached the top of the needle hub 6. In an alternative embodiment (not shown), a stopping means located on the inside wall of the body element 2 is provided, the stopping means being configured to stop the movement of the needle unit 8.

The spring element 11 serves as resistance element for slowing down the priming process so that the distal part of the needle 9 remains sufficient time in the cartridge for relieving the pressure of the cartridge. The spring element 11 slows down the movement of the button element 7 due to the elastic resilience of the spring element 11, the elastic resilience counteracting against the pushing force 41.

Figure 4:
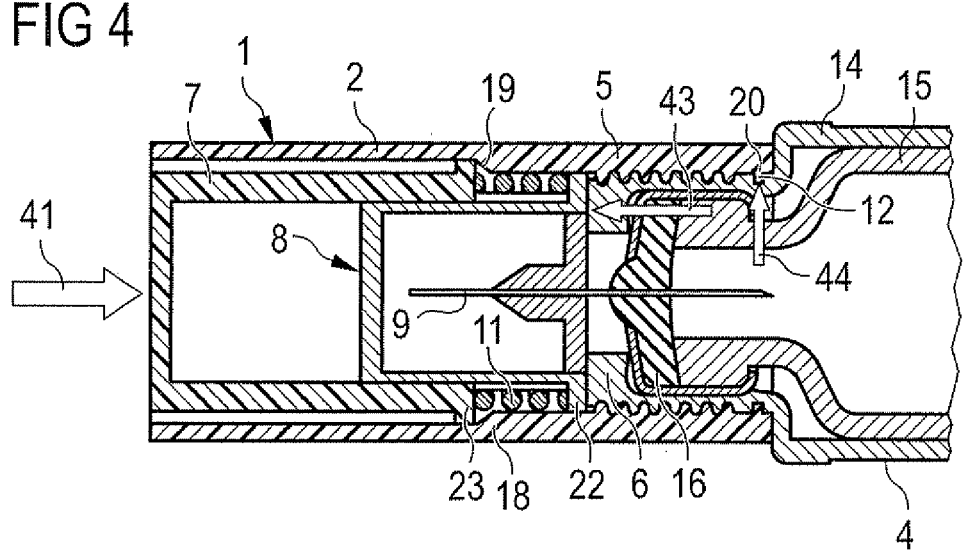

FIG. 4 shows that the movement of the distal end of the spring element 11 is also stopped when the distal movement of the needle unit 8 is stopped. When the needle unit 8 reaches the needle hub 6, a counterforce, which is indicated by an arrow 43, impacts proximally to the distal end of the spring element 11. Due to the counterforce 43 and the pushing force 41 transferred by the moving button element 7 the spring element 11 is compressed when the button element 7 is distally moved further with respect to the body element 2 and the needle unit 8. Thus, the needle unit 8 is inserted to the button element 7.

The spring element 11 is compressed until the distal edge 23 of the button element reaches the mating means 18, as shown in FIG. 4.

Figure 5:
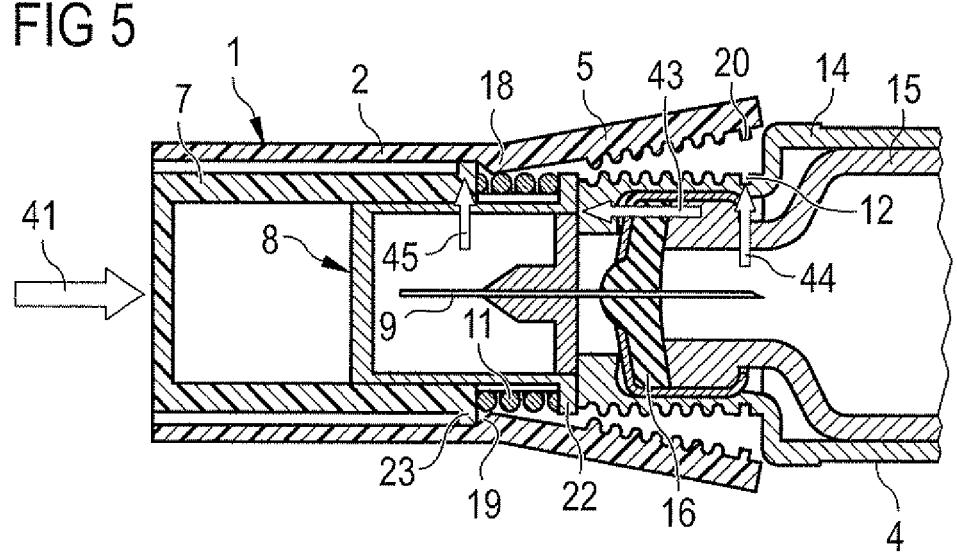

FIG. 5 shows that the distal edge 23 of the button element is pushed towards the chamfer 19 of the mating means 18 (as indicated by an arrow 45). Thus, the mating means 18 moves outwards. Due to the leverage effect the elongated snapping means 5 moves outwards also so that the joint part 20 located at the distal end of the snapping means 5 is detached from the groove 12 located in the needle hub 6 (as indicated by an arrow 44).

When the snapping connection between the joint part 20 and the groove 12 is disconnected, the needle assembly 1 is unlocked and can be removed from the medication delivery device 4. When the needle assembly 1 is being removed the needle is extricated from the membrane 11. Due to the elastic resilience of the spring element 11 the needle 9 retreats to the body element 2 when the button element 7 is not pushed any more.

One embodiment of the needle assembly is a single use needle assembly which is delivered after priming. An alternative embodiment is reusable.

Other implementations are within the scope of the claims. Elements of different embodiments may be combined to form implementations not specifically described herein.

The invention claimed is:

1. Needle assembly having distal and proximal ends, the needle assembly comprising:

a body element having distal and proximal ends;

an attachment located at the distal end of the body element, the attachment configured to be attached to a distal end of a medication delivery device comprising a cartridge containing medication;

a button element located at the proximal end of the body element, wherein the button element is movable within and relative to the body element in a distal direction toward the distal end of the medication delivery device from a first position to a second position;

a needle configured to move in the distal direction toward the cartridge, when the button element is moved in the distal direction from the first position to the second position;

wherein, in a first state, the attachment is locked and, in a second state, the attachment is unlocked; and wherein the attachment is unlocked when the button element reaches a second predetermined position.

2. Needle assembly according to claim 1, comprising a medication trap.

3. Needle assembly according to claim 2, wherein the medication trap is formed as a tank surrounding a proximal part of the needle.

4. Needle assembly according to claim 1, wherein the attachment comprises a snap.

5. Needle assembly according to claim 1, comprising a resistance element configured to counteract against movement of the button element.

6. Needle assembly according to claim 5, wherein the resistance element is configured to counteract against a distal movement of the button element when a needle unit which comprises the needle reaches a first predetermined position.

7. Needle assembly according to claim 6, comprising a stop configured to stop the distal movement of the needle when the needle unit has reached the first predetermined position.

8. Needle assembly according to claim 5, wherein the resistance element is formed as spring element.

9. Needle assembly according to a claim 1, wherein the body element has a distal part and a proximal part, the distal part forming the attachment, wherein the button element is moveable in the distal direction with respect to the attachment.

10. Needle assembly according to claim 9, wherein the button element can be pushed into the body element, and wherein a stop is formed as a protrusion, the stop being located on the inside wall of the body element.

11. Medication delivery system comprising a medication delivery device and the needle assembly of claim 1, the needle assembly being attached to the medication delivery device.

12. Medication delivery system according to claim 11, wherein the medication delivery device comprises a needle hub, wherein a cartridge containing medication has a membrane, the needle hub being releasably connected with the attachment.

13. Medication delivery system according to claim 12, wherein the needle does not puncture the membrane if the button element is in the first position, and wherein the needle punctures the membrane when the button element is moved to the second position.

14. Medication delivery system according to claim 11, wherein the needle assembly is detachable in the second position.

15. Medication delivery system according to claim 14, wherein the attachment comprises a snap; and wherein in a first state the snap is engaged with the needle hub and in a second state the snap is disengaged from the needle hub.

* * * * *